(12) United States Patent
George et al.

(10) Patent No.: US 10,828,080 B2
(45) Date of Patent: *Nov. 10, 2020

(54) REGULATING PRESSURE TO LOWER TEMPERATURE IN A CRYOTHERAPY BALLOON CATHETER

(71) Applicant: Boston Scientific Scimed, Inc., Maple Grove, MN (US)

(72) Inventors: Leonard J. George, Scotts Valley, CA (US); Joann Heberer, Portola Valley, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 461 days.

This patent is subject to a terminal disclaimer.

(21) Appl. No.: 15/729,039

(22) Filed: Oct. 10, 2017

(65) Prior Publication Data

US 2018/0028251 A1    Feb. 1, 2018

Related U.S. Application Data

(63) Continuation of application No. 14/502,813, filed on Sep. 30, 2014, now Pat. No. 9,801,676, which is a (Continued)

(51) Int. Cl.
*A61B 18/02* (2006.01)
*A61B 17/00* (2006.01)
*A61B 18/00* (2006.01)

(52) U.S. Cl.
CPC .... *A61B 18/02* (2013.01); *A61B 2017/00017* (2013.01); *A61B 2017/00539* (2013.01); (Continued)

(58) Field of Classification Search
CPC .......... A61B 18/02; A61B 2017/00017; A61B 2017/00539; A61B 2018/00023; (Continued)

(56) References Cited

U.S. PATENT DOCUMENTS

| 3,125,096 A | 3/1964 | Antiles et al. |
| 3,459,731 A | 8/1969 | Gramera et al. |

(Continued)

FOREIGN PATENT DOCUMENTS

| WO | 9105528 A1 | 5/1991 |
| WO | 9838934 A1 | 9/1998 |

OTHER PUBLICATIONS

Gage et al., "Freezing injury to large blood vessels in dogs," Surgery, 61(5); 748-754, May 1967.

*Primary Examiner* — Michael F Peffley
(74) *Attorney, Agent, or Firm* — Faegre Drinker Biddle & Reath LLP (57) ABSTRACT

A cryotherapy catheter can include an elongate member and an inflatable balloon at a distal end of the elongate member, the elongate member having lumens formed therein to supply cryogenic fluid to a chamber of the balloon and to channel exhaust from the balloon chamber; and a controller programmed to control a first rate at which the cryogenic fluid is supplied to the balloon chamber and a second rate at which exhaust is channeled from the balloon chamber, wherein the controller is programmed to a) develop, during a first phase of a cryotherapy procedure, a first pressure inside the balloon chamber at a value that is greater than an ambient pressure outside and adjacent to a proximal end of the elongate member, and b) develop, during a second phase of the cryotherapy procedure, the first pressure at a value that is less than the ambient pressure.

16 Claims, 8 Drawing Sheets

Related U.S. Application Data continuation of application No. 12/542,978, filed on Aug. 18, 2009, now Pat. No. 8,845,627.

(60) Provisional application No. 61/090,985, filed on Aug. 22, 2008.

(52) U.S. Cl.
CPC ............... *A61B 2018/0022* (2013.01); *A61B 2018/00023* (2013.01); *A61B 2018/0212* (2013.01); *A61B 2018/0262* (2013.01)

(58) Field of Classification Search
CPC .... A61B 2018/0022; A61B 2018/0212; A61B 2018/0262
See application file for complete search history.

(56) References Cited

U.S. PATENT DOCUMENTS

| | | |
|---|---|---|
| 3,901,241 A | 8/1975 | Allen et al. |
| 4,336,691 A | 6/1982 | Burstein et al. |
| 4,383,992 A | 5/1983 | Lipari |
| 4,478,995 A | 10/1984 | Shinoda et al. |
| 4,497,803 A | 2/1985 | Harada et al. |
| 4,535,152 A | 8/1985 | Szejtli et al. |
| 4,596,795 A | 6/1986 | Pitha |
| 4,659,696 A | 4/1987 | Hirai et al. |
| 4,727,064 A | 2/1988 | Pitha |
| 4,754,752 A | 7/1988 | Ginsburg |
| 4,764,604 A | 8/1988 | Muller |
| 4,870,060 A | 9/1989 | Muller |
| 5,019,075 A | 5/1991 | Spears |
| 5,041,089 A | 8/1991 | Muller et al. |
| 5,078,713 A | 1/1992 | Varney |
| 5,083,549 A | 1/1992 | Cho et al. |
| 5,092,841 A | 3/1992 | Spears |
| 5,106,360 A | 4/1992 | Ishiwara et al. |
| 5,106,837 A | 4/1992 | Carson et al. |
| 5,147,355 A | 9/1992 | Friedman et al. |
| 5,151,100 A | 9/1992 | Abele et al. |
| 5,190,539 A | 3/1993 | Fletcher |
| 5,191,883 A | 3/1993 | Lennox et al. |
| 5,196,024 A | 3/1993 | Barath |
| 5,224,943 A | 7/1993 | Goddard |
| 5,275,595 A | 1/1994 | Dobak, III |
| 5,310,732 A | 5/1994 | Carson et al. |
| 5,328,480 A | 7/1994 | Melker et al. |
| 5,401,724 A | 3/1995 | Beutler |
| 5,424,296 A | 6/1995 | Saven et al. |
| 5,458,612 A | 10/1995 | Chin |
| 5,486,208 A | 1/1996 | Ginsburg |
| 5,501,681 A | 3/1996 | Neuwirth et al. |
| 5,506,214 A | 4/1996 | Beutler |
| 5,510,336 A | 4/1996 | Saven et al. |
| 5,545,195 A | 8/1996 | Lennox et al. |
| 5,617,739 A | 4/1997 | Little |
| 5,624,392 A | 4/1997 | Saab |
| 5,644,502 A | 7/1997 | Little |
| 5,706,810 A | 1/1998 | Rubinsky et al. |
| 5,733,280 A | 3/1998 | Avitall |
| 5,746,736 A | 5/1998 | Tankovich |
| 5,758,505 A | 6/1998 | Dobak, III et al. |
| 5,800,487 A | 9/1998 | Mikus et al. |
| 5,868,673 A | 2/1999 | Vesely |
| 5,868,735 A | 2/1999 | Lafontaine |
| 5,885,276 A | 3/1999 | Ammar et al. |
| 5,899,898 A | 5/1999 | Arless et al. |
| 5,902,268 A | 5/1999 | Saab |
| 5,902,299 A | 5/1999 | Jayaraman |
| 5,957,963 A | 9/1999 | Dobak, III |
| 5,971,979 A | 10/1999 | Joye et al. |
| 5,993,444 A | 11/1999 | Ammar et al. |
| 6,011,995 A | 1/2000 | Guglielmi et al. |
| 6,015,390 A | 1/2000 | Krag |
| 6,106,518 A | 8/2000 | Wittenberger et al. |
| 6,161,543 A | 12/2000 | Cox et al. |
| 6,171,249 B1 | 1/2001 | Chin et al. |
| 6,174,873 B1 | 1/2001 | Wrenn, Jr. et al. |
| 6,182,666 B1 | 2/2001 | Dobak, III |
| 6,194,395 B1 | 2/2001 | Schultz et al. |
| 6,235,019 B1 | 5/2001 | Lehmann et al. |
| 6,239,118 B1 | 5/2001 | Schatz et al. |
| 6,261,312 B1 | 7/2001 | Dobak, III et al. |
| 6,283,959 B1 | 9/2001 | Lalonde et al. |
| 6,290,686 B1 | 9/2001 | Tanzer |
| 6,290,696 B1 | 9/2001 | Lafontaine |
| 6,355,029 B1 | 3/2002 | Joye et al. |
| 6,407,079 B1 | 6/2002 | Muller et al. |
| 6,428,534 B1 | 8/2002 | Joye et al. |
| 6,494,844 B1 | 12/2002 | Van Bladel et al. |
| 6,514,245 B1 * | 2/2003 | Williams ............... A61B 18/02 128/898 |
| 6,517,533 B1 | 2/2003 | Swaminathan |
| 6,540,740 B2 | 4/2003 | Lehmann et al. |
| 6,540,771 B2 | 4/2003 | Dobak, III et al. |
| 6,547,784 B1 | 4/2003 | Thompson et al. |
| 6,575,966 B2 | 6/2003 | Lane et al. |
| 6,602,246 B1 | 8/2003 | Joye et al. |
| 6,626,902 B1 | 9/2003 | Kucharczyk et al. |
| 6,629,972 B2 | 10/2003 | Lehmann et al. |
| 6,641,564 B1 | 11/2003 | Kraus |
| 6,652,565 B1 | 11/2003 | Shimada et al. |
| 6,682,525 B2 | 1/2004 | Lalonde et al. |
| 6,699,849 B1 | 3/2004 | Loftsson et al. |
| 6,706,037 B2 | 3/2004 | Zvuloni et al. |
| 6,755,822 B2 | 6/2004 | Reu et al. |
| 6,913,604 B2 | 7/2005 | Mihalik et al. |
| 6,942,659 B2 | 9/2005 | Lehmann et al. |
| 6,955,174 B2 | 10/2005 | Joye et al. |
| 6,981,382 B2 | 1/2006 | Lentz et al. |
| 7,060,062 B2 * | 6/2006 | Joye ..................... A61B 18/02 606/21 |
| 7,135,034 B2 | 11/2006 | Friedman et al. |
| 7,261,730 B2 | 8/2007 | Friedman et al. |
| 7,303,554 B2 | 12/2007 | Lalonde et al. |
| 7,354,434 B2 | 4/2008 | Zvuloni et al. |
| 7,357,797 B2 | 4/2008 | Ryba |
| 7,481,806 B2 | 1/2009 | Levin |
| 7,499,206 B1 | 3/2009 | Richardson |
| 7,625,369 B2 | 12/2009 | Abboud et al. |
| 7,731,711 B2 | 6/2010 | Levin |
| 7,753,905 B2 | 7/2010 | Lehmann et al. |
| 7,777,130 B2 | 8/2010 | Deborski et al. |
| 8,128,617 B2 * | 3/2012 | Bencini ................ A61B 18/02 606/21 |
| 2002/0010460 A1 | 1/2002 | Joye et al. |
| 2002/0032438 A1 * | 3/2002 | Lafontaine ............ A61B 18/02 606/21 |
| 2002/0045892 A1 | 4/2002 | Kramer |
| 2002/0045894 A1 | 4/2002 | Joye et al. |
| 2004/0034344 A1 | 2/2004 | Ryba |
| 2005/0198972 A1 | 9/2005 | Lentz et al. |
| 2005/0245943 A1 * | 11/2005 | Zvuloni .................... F25B 9/02 606/121 |
| 2007/0250050 A1 | 10/2007 | Lafontaine |
| 2009/0299356 A1 * | 12/2009 | Watson ............... A61M 25/1011 606/21 |

* cited by examiner

After 50 Seconds

FIG. 4A

After 50 Seconds

FIG. 4D

After 100 Seconds

FIG. 4B

After 100 Seconds

FIG. 4E

After 150 Seconds

FIG. 4C

After 150 Seconds

FIG. 4F

After 50 Seconds

FIG. 4G

After 100 Seconds

FIG. 4H

After 150 Seconds

REGULATING PRESSURE TO LOWER TEMPERATURE IN A CRYOTHERAPY BALLOON CATHETER

CROSS-REFERENCE TO RELATED APPLICATIONS

This application is a continuation of co-pending U.S. application Ser. No. 14/502,813, filed Sep. 30, 2014, now U.S. Pat. No. 9,801,676, which is a continuation of U.S. application Ser. No. 12/542,978, filed Aug. 18, 2009, now U.S. Pat. No. 8,845,627, which claims priority to U.S. Provisional Patent Application Ser. No. 61/090,985, filed on Aug. 22, 2008, the entire contents of which are hereby incorporated by reference.

BACKGROUND

A number of serious medical conditions may be treated in a minimally invasive manner with various kinds of catheters designed to reach treatment sites internal to a patient's body. One such medical condition is atrial fibrillation—a condition that results from abnormal electrical activity within the heart. This abnormal electrical activity may originate from various focal centers of the heart and generally decreases the efficiency with which the heart pumps blood. It is believed that some of these focal centers reside in the pulmonary veins of the left atrium. It is further believed that atrial fibrillation can be reduced or controlled by structurally altering or ablating the tissue at or near the focal centers of the abnormal electrical activity.

One method of ablating tissue of the heart and pulmonary veins to treat atrial fibrillation is cryotherapy—the extreme cooling of body tissue. Cryotherapy may be delivered to appropriate treatment sites inside a patient's heart and circulatory system by a cryotherapy catheter. A cryotherapy catheter generally includes a treatment member at its distal end, such as an expandable balloon having a cooling chamber inside. A cryogenic fluid may be provided by a source external to the patient at the proximal end of the cryotherapy catheter and delivered distally through a lumen to the cooling chamber where it is released. Release of the cryogenic fluid into the chamber cools the chamber (e.g., through the Joule-Thomson effect), and correspondingly, the balloon's outer surface, which is in contact with tissue that is to be ablated. Gas resulting from release of the cryogenic fluid may be exhausted proximally through an exhaust lumen to a reservoir or pump external to the patient.

SUMMARY

In a cryotherapy balloon catheter in which cryogenic fluid is delivered to and released in a balloon portion, where it undergoes a phase change that cools the balloon portion by the Joule-Thomson effect, pressure inside the balloon can affect the boiling point of the cryogenic fluid, and thus the temperature to which the balloon portion can be cooled. In some implementations, lowering the pressure inside the balloon portion results in a lower temperature, which can accelerate a cryotherapy procedure. Some cryotherapy procedures include two phases: an initial treatment phase during which the cryotherapy balloon is inflated against body tissue that is to be treated (e.g., the ostium of a pulmonary vein) and cooled enough to cause its surface to be frozen to the body tissue; and a second treatment phase during which the pressure can be lowered inside the balloon, resulting in a lower surface temperature of the balloon, which may accelerate the cryotherapy procedure.

In some implementations, a method of performing a cryotherapy procedure can include introducing a cryotherapy balloon catheter at a treatment site inside a patient's body; regulating, during a first phase of a cryotherapy procedure, flow of cryogenic fluid to and exhaust from a distal balloon portion of the cryotherapy balloon catheter to cause a) a first pressure to be reached inside the distal balloon portion that is sufficiently high to cause an outer wall of the distal balloon portion to be pressed against body tissue at the treatment site, and b) a first temperature to be reached inside the distal balloon portion that is sufficiently low to cause the body tissue to freeze to the outer wall; and regulating, during a second phase of the cryotherapy procedure, flow of cryogenic fluid to and exhaust from the distal balloon portion to reduce pressure inside the distal balloon portion to a second pressure that is less than the first pressure, causing a temperature inside the distal portion to reach a second temperature that is below the first temperature.

The cryotherapy balloon catheter can be configured to enable Joule-Thomson cooling inside the distal balloon portion when cryogenic fluid is delivered to the distal balloon portion and resulting gas is exhausted from the distal balloon portion. In some implementations, the first temperature can be less than 0° C. In some implementations, the second temperature can be between −89° C. and −91° C. Regulating the flow of cryogenic fluid to and exhaust from the distal balloon portion can include regulating the flows such that heat is extracted from the body tissue at a greater rate during the second phase than a rate at which heat is extracted from the body tissue during the first phase.

In some implementations, the first pressure is approximately five pounds per square inch (PSI) above ambient pressure. In some implementations, the first pressure is approximately 5-25 PSI above ambient pressure. Ambient pressure may be characterized by atmospheric air pressure adjacent to the patient's body. The second pressure can be approximately equal to ambient pressure. The second pressure can be negative relative to ambient pressure. The second pressure can be maintained at a value that is sufficient to prevent the outer wall from being peeled away from the body tissue by vacuum forces inside the distal balloon portion or by elastic forces of material that makes up the distal balloon portion. The method can further include inflating the distal balloon portion.

The method can further include regulating, after the second phase, the flow of cryogenic fluid to and exhaust from the distal balloon portion such that minimal heat is extracted from the body tissue, allowing the body tissue to warm up. The method can further include deflating the distal balloon portion, introducing the cryotherapy balloon catheter to a second treatment site, and regulating the flow of cryogenic fluid to and exhaust from the distal balloon portion to repeat the first and second phases of the cryotherapy procedure at the second treatment site. Regulating flow of cryogenic fluid to and exhaust from the distal balloon portion can include regulating flow of liquid nitrous oxide to the distal balloon portion and flow of gaseous nitrous oxide from the distal balloon portion.

In some implementations, a cryotherapy catheter includes an elongate member and an inflatable balloon at a distal end of the elongate member, the elongate member having lumens formed therein to supply cryogenic fluid to a chamber of the balloon and to channel exhaust from the balloon chamber; and a controller programmed to control a first rate at which the cryogenic fluid is supplied to the balloon chamber and a second rate at which exhaust is channeled from the balloon chamber, wherein the controller is programmed to a) develop, during a first phase of a cryotherapy procedure, a first pressure inside the balloon chamber at a value that is greater than a second pressure outside and adjacent to a proximal end of the elongate member, and b) develop, during a second phase of the cryotherapy procedure, the first pressure at a value that is less than the second pressure. The second pressure can be an ambient pressure, wherein the ambient pressure can be characterized as atmospheric air pressure adjacent to the patient's body.

In some implementations, the controller is programmed to supply cryogenic fluid to the balloon chamber such that the cryogenic fluid boils at a first temperature in an environment of the first pressure, and boils at a second temperature, which is lower than the first temperature, at pressures that are less than the second pressure.

In some implementations, a cryotherapy catheter includes an elongate member and an inflatable balloon at a distal end of the elongate member, the elongate member having lumens formed therein to supply cryogenic fluid to a chamber of the balloon and to channel exhaust from the balloon chamber; and a controller programmed to control a first rate at which the cryogenic fluid is supplied to the balloon chamber and a second rate at which exhaust is channeled from the balloon chamber, wherein the controller is programmed to a) develop, during a first phase of a cryotherapy procedure, a first pressure inside the balloon chamber at a value that is greater than an ambient pressure outside and adjacent to a proximal end of the elongate member, and b) develop, during a second phase of the cryotherapy procedure, a second pressure inside the balloon chamber at a value that is less than the first pressure. The inflatable balloon can be configured to be disposed inside a lumen or body cavity of a human patient to deliver cryotherapy to tissue of the lumen or body cavity.

The details of one or more implementations are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

In a cryotherapy balloon catheter in which cryogenic fluid is delivered to and released in a balloon portion, where it undergoes a phase change that cools the balloon portion by the Joule-Thomson effect, pressure inside the balloon can affect the boiling point of the cryogenic fluid, and thus the temperature to which the balloon portion can be cooled. In some implementations, lowering the pressure inside the balloon portion results in a lower temperature, which can accelerate a cryotherapy procedure. Some cryotherapy procedures include two phases: an initial treatment phase during which the cryotherapy balloon is inflated against body tissue that is to be treated (e.g., the ostium of a pulmonary vein) and cooled enough to cause its surface to be frozen to the body tissue; and a second treatment phase during which the pressure can be lowered inside the balloon, resulting in a lower surface temperature of the balloon, which may accelerate the cryotherapy procedure.

Figure 1A:
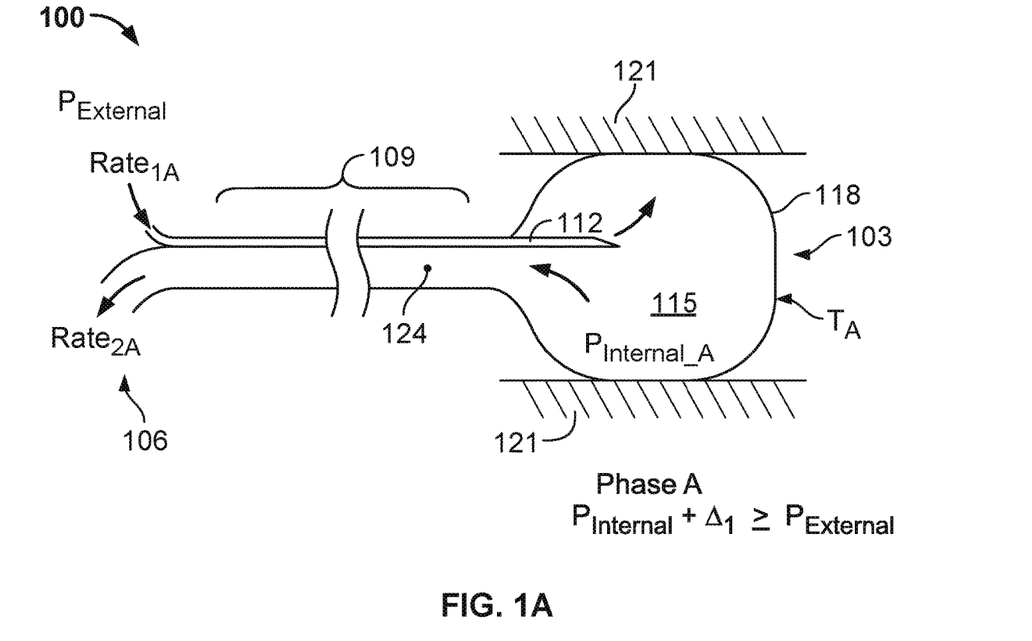
FIGS. 1A and 1B illustrate details of an example cryotherapy balloon catheter that can be used to deliver cryotherapy to body tissue in first and second treatment phases, respectively.
Figure 1B:
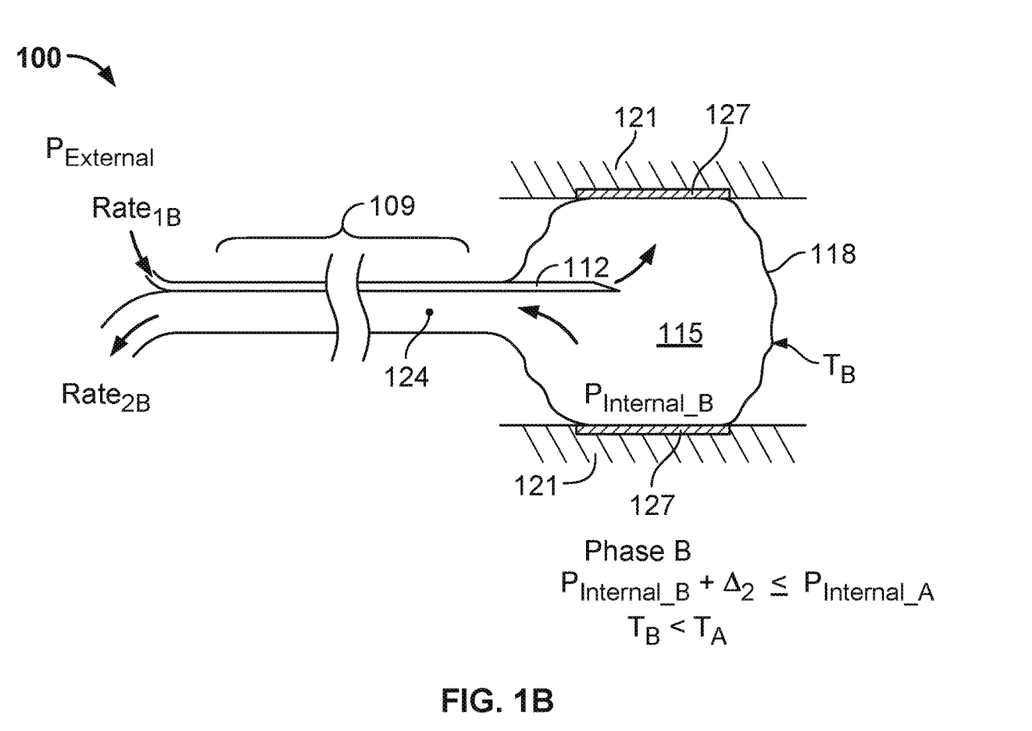

FIGS. 1A and 1B illustrate example details of a cryotherapy balloon catheter 100 that can be used to deliver cryotherapy, and FIGS. 1A and 1B further depict an example first treatment phase (FIG. 1A) and second treatment phase (FIG. 1B) during which cryotherapy can be provided to body tissue. Additional details of an example cryotherapy balloon catheter are described below with reference to FIGS. 7 and 8A-8C.

The cryotherapy balloon catheter 100 of FIGS. 1A and 1B has a distal cryotherapy balloon 103 that can be inserted into a body lumen of a patient, such as, for example, a blood vessel or other internal body structure. More particularly, for example, the distal cryotherapy balloon 103 can be inserted (in a deflated state), through appropriate blood vessels, into a patient's heart, and specifically into the patient's left atrium. Once in the patient's left atrium, the cryotherapy balloon can be employed to ablate tissue of the pulmonary veins (e.g., tissue at the ostium of one or more pulmonary veins) in order to eliminate aberrant electrical signals that may be causing atrial fibrillation in the patient. Similarly, the cryotherapy balloon catheter 100 can be routed to other treatment sites inside a patient and employed to treat other conditions. During whatever treatment is performed, a proximal end 106 of the cryotherapy balloon catheter remains outside the patient.

Between the proximal end 106 and the distal cryotherapy balloon 103 is an elongate member 109 (e.g., a catheter shaft) having various internal lumens, including a supply lumen 112 for delivering a cryogenic fluid to the distal cryotherapy balloon 103. The cryogenic fluid can be released into a chamber 115 of the balloon 103, where it undergoes a phase change to a gas. As a result of the phase change, heat is extracted from the surroundings of the chamber 115, thereby cooling the surface 118 of the balloon 103 and body tissue 121 that is in contact with the surface 118 (e.g., via the Joule-Thomson effect). The elongate member 109 also includes an exhaust lumen 124 for exhausting the resulting gas from the chamber 115.

Figure 2:
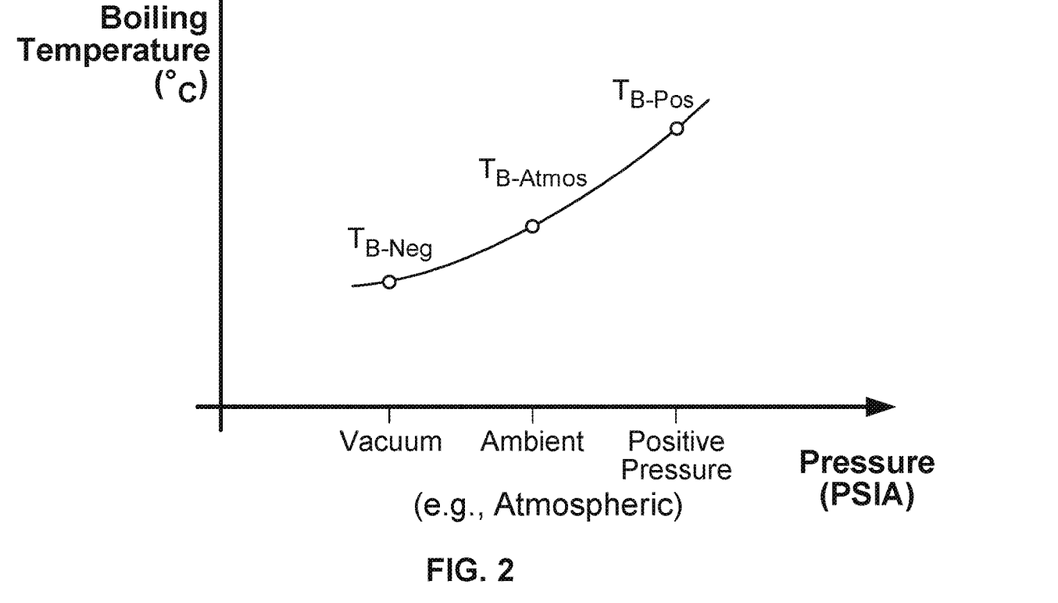
FIG. 2 is a graph illustrating example relationships between pressure and boiling point of a cryogenic fluid that can be used with the cryotherapy balloon catheter shown in FIGS. 1A and 1B.

Pressure inside the chamber 115, $P_{INTERNAL\_A}$, can affect the temperature at which the cryogenic fluid changes state from a liquid to a gas (e.g., the boiling point). That is, with brief reference to FIG. 2, the cryogenic fluid may have one boiling temperature at atmospheric pressure, $T_{B\_ATMOS}$, another, higher boiling temperature, $T_{B\_POS}$, at a higher pressure; and another, lower boiling temperature, $T_{B\_NEG}$, at a lower pressure. By raising the pressure inside the chamber 115, the boiling temperature of the cryogenic fluid (and thus the temperature that can be achieved at the surface 118) can be increased; by lowering the pressure inside the chamber 115, the boiling temperature can be decreased.

In some implementations, as will now be described in greater detail, a cryotherapy procedure can include a first treatment phase in which pressure inside the chamber 115 is higher than pressure inside the chamber 115 during the second treatment phase. In such implementations, pressure during the first treatment phase may be sufficient to inflate the balloon 103 and establish firm contact between the balloon 103 and body tissue 121 to be treated. A layer of ice can form between the body tissue 121 and the balloon 103 during the first treatment phase, freezing the body tissue 121 to the balloon surface 118. In the second treatment phase, pressure can be reduced to lower the temperature (e.g., to accelerate the cryotherapy procedure), and the layer of ice can cause the tissue 121 to remain adhered to the balloon surface 118.

During the first treatment phase (Phase A), as depicted in FIG. 1A, an internal balloon pressure, $P_{INTERNAL\_A}$, can be developed to a value that is greater than ambient pressure at the proximal end 106 of the cryotherapy catheter 100. As used herein, ambient pressure can refer to atmospheric pressure at the location of the patient being treated with the cryotherapy catheter (that is, atmospheric pressure given the altitude of the patient and other pressure-determining characteristics of the air immediately surrounding the patient). Thus, when the balloon 103 is outside of a patient (and not subject to compressive forces other than atmospheric pressure and elastic forces of the balloon itself), the balloon 103 will generally inflate when the pressure inside the chamber 115 is greater than the ambient pressure. Conversely, the balloon 103 will generally not inflate when the pressure inside the chamber 115 is less than ambient pressure. Additional pressure (above ambient pressure) may be required to inflate the balloon 103 inside the patient. For example, additional pressure may be needed to overcome pressure exerted by tissue against which the balloon 103 is expanding (e.g., tissue of the patient's pulmonary vein), pressure exerted by blood flow against the balloon 103, or other pressures exerted by the patient's body or the balloon material itself.

Maintaining $P_{INTERNAL\_A}$ greater than $P_{EXTERNAL}$ during the first treatment phase can enable the balloon 103 to be inflated, such that its outer surface 118 maintains contact with adjacent body tissue 121. To ensure good contact, $P_{INTERNAL\_A}$ may be greater than $P_{EXTERNAL}$ by some margin, $\Delta_1$. For example, in some implementations, $P_{INTERNAL\_A}$ is maintained at approximately (e.g., within 5%, 10%, or 25%) 5 PSI above $P_{EXTERNAL}$ so that the balloon 103 exerts sufficient force against the adjacent tissue 121. In other implementations, a greater margin is maintained, such as approximately (e.g., within 5%, 10%, or 25%) 10, 15, 20, or 25 PSI. As shown in FIG. 1A, the relationship between pressures inside and outside the chamber 115 may be expressed as $P_{INTERNAL\_A}+\Delta_1>=P_{EXTERNAL}$.

In some implementations, $P_{INTERNAL\_A}$ is regulated by controlling either or both of the rates at which cryogenic fluid is introduced into the chamber 115 (or correspondingly, the rate at which the cryogenic fluid is introduced into the supply lumen 112, $RATE_{1A}$) and the rate at which exhaust is channeled from the chamber 115, $RATE_{2A}$. The control may be accomplished, for example, by a controller, one or more valves, and one or more pumps, as described below with reference to FIG. 7. In some implementations, $P_{INTERNAL\_A}$ can be primarily controlled by regulating $RATE_{2A}$. That is, $RATE_{2A}$ may have a much greater affect on $P_{INTERNAL\_A}$ than $RATE_{1A}$, and accordingly, $RATE_{2A}$ may be precisely controlled with a closed loop control system. $RATE_{1A}$, on the other hand, may be less precisely controlled with an open-loop control system.

In some implementations, the first phase of cryotherapy that is depicted in FIG. 1A may be relatively short in duration relative to a second phase, and may serve primarily to freeze the adjacent tissue 121 to the surface 118 of the balloon 103. Once the adjacent tissue 121 is frozen to the surface 118, contact between the tissue 121 and surface 118 can be maintained by a layer of ice (element 127 in FIG. 1B) between the tissue 121 and surface 118, even if the pressure inside the chamber 115 is reduced. An example second treatment phase is now described in more detail with reference to FIG. 1B.

FIB. 1B depicts a second phase of cryotherapy during which the pressure inside the chamber 115, $P_{INTERNAL\_B}$, may be reduced relative to $P_{EXTERNAL}$ (e.g., in order to lower the boiling temperature of the cryogenic fluid and the corresponding temperature, $T_B$, on the surface 118 of the balloon 103). In particular, as depicted, $P_{INTERNAL\_B}$ may be less than $P_{INTERNAL\_A}$ by some threshold, $\Delta_2$. That is, in some implementations, $P_{INTERNAL\_B}\Delta_2<=P_{INTERNAL\_A}$.

In some implementations, $P_{INTERNAL\_B}$ is close to, but still greater than, ambient pressure (e.g., positive relative to $P_{EXTERNAL}$). In other implementations, $P_{INTERNAL\_B}$ is negative relative to $P_{EXTERNAL}$. That is, in the latter implementations, a partial vacuum may be maintained in the chamber 115. In any case, the lower pressure inside the chamber 115 during the second treatment phase, relative to the first treatment phase, results in a lower temperature, $T_B$, at the surface 118, than the temperature $T_A$ at the surface 118 in the first treatment phase. The lower pressure in the second treatment phase is graphically depicted by the partially deflated appearance of the balloon 103 in FIG. 1B.

Even though the balloon 103 may be partially deflated in the second treatment phase, contact between the surface 118 of the balloon 103 and adjacent tissue 121 can be maintained by the layer of ice 127 formed during the first treatment phase. This contact can be maintained as long as the attractive force of the ice 127 is greater than any elastic force of the balloon 103 and any vacuum force created by the pressure inside the chamber 115, both of which may tend to draw the surface 118 of the balloon 103 away from the tissue 121. That is, although $P_{INTERNAL\_B}$ may be lower than $P_{INTERNAL\_A}$, $P_{INTERNAL\_B}$ may still need to be maintained above a level at which the balloon surface is peeled away from the tissue 121 by a force that exceeds the attractive force of the ice 127.

Figure 3:
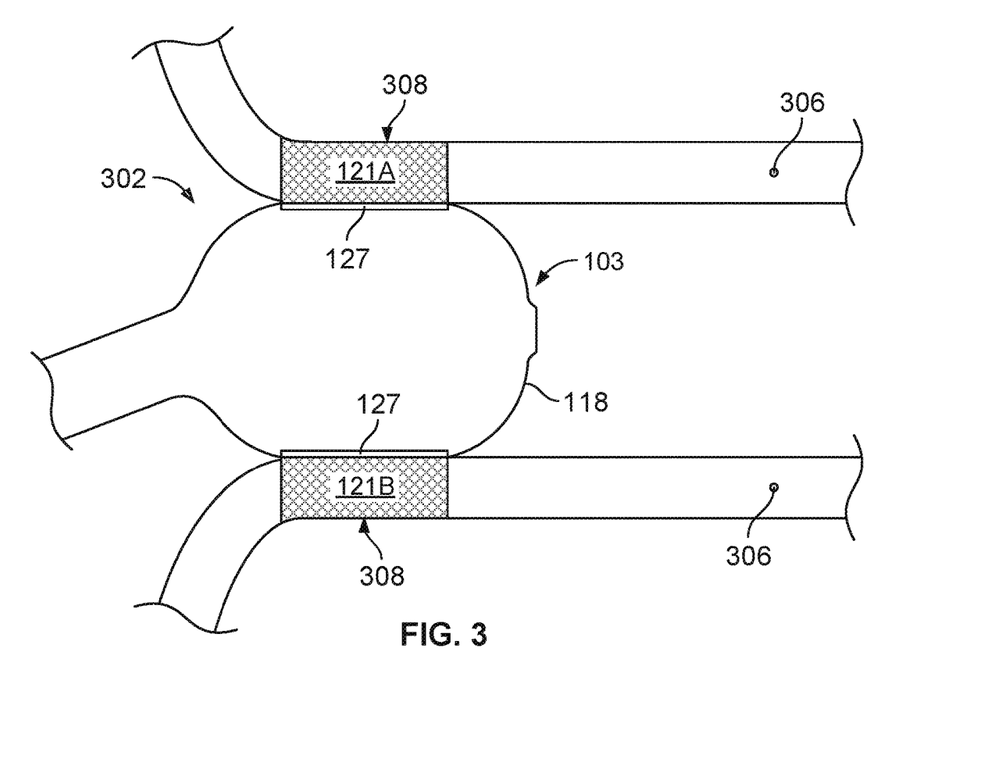
FIG. 3 illustrates the cryotherapy balloon of FIGS. 1A and 1B positioned adjacent to body tissue that is to be treated.

FIG. 3 illustrates another view of the cryotherapy balloon 103, positioned to deliver cryotherapy to the body tissue 121. For purposes of example, the tissue 121 will be described and depicted as corresponding to the ostium 302 of a pulmonary vein 306 in the heart of a patient, but the reader will appreciate that the cryotherapy balloon 103 can be employed to deliver cryotherapy to other body structures (e.g., arteries or veins; lymph nodes; other body lumens, cavities, or glands, etc.).

During an example cryotherapy treatment, the above-described process of allowing cryogenic fluid to undergo a phase change inside the balloon 103 causes Joule-Thomson cooling of the surface 118 of the balloon 103 and corresponding ablation of the adjacent tissue in regions 121A and 121B. As depicted in FIG. 3 and described above with reference to FIGS. 1A and 1B, a layer of ice 127 may form between the balloon 103 and the tissue 121A and 121B. Ice may also form within the tissue itself, in regions 121A and 121B.

In some implementations, ablation (e.g., permanent and therapeutic alteration or remodeling of the tissue in regions 121A and 121B) occurs when the tissue reaches a certain temperature. For example, tissue of human pulmonary veins may begin to be ablated around −10° C. In some procedures, it may be desirable to cool the tissue by some margin beyond the temperature at which it begins to be ablated. More particularly, for example, it may be desirable to cool the tissue to −20° C. Moreover, it may be desirable to cool the entire region of tissue to the desired temperature—that is, the entire thickness of the pulmonary vein 306 in this example. In order to cool the entire thickness of the pulmonary vein at regions 121A and 121B, the surface of the balloon should generally be much cooler than the desired therapeutic temperature. Thus, for example, to cool the outer wall 308 of the pulmonary vein to −20° C., the temperature of the surface 118 of the balloon may be maintained at −60° C. or lower, for some period of time.

Generally, the greater the temperature difference between the surface 118 of the balloon 103 and the body tissue 121A and 121B being treated, the faster heat is extracted from the body tissue 121A and 121B. Thus, to facilitate as short a cryotherapy procedure as possible, it may be desirable maintain the surface 118 at very low temperatures. This may be particularly true in light of dynamics in play as the tissue 121A and 121B is cooled. In particular, the tissue in regions 121A and 121B may cool at a non-uniform rate. For example, the tissue 121A and 121B may cool at one rate until portions freeze, at which point, heat may be conducted within the frozen portions differently (e.g., some tissue may act as an insulator against further heat flow once it is frozen; other tissue may conduct heat better once frozen). Other dynamics may also affect how the tissue 121A and 121B cools, such as, for example, heat released by metabolic processes inside the tissue 121A and 121B, or heat flow resulting from blood perfusion within the tissue 121A and 121B. Heat flow within the body tissue 121A and 121B is now described in more detail with reference to FIGS. 4A-4I.

Figure 4A:
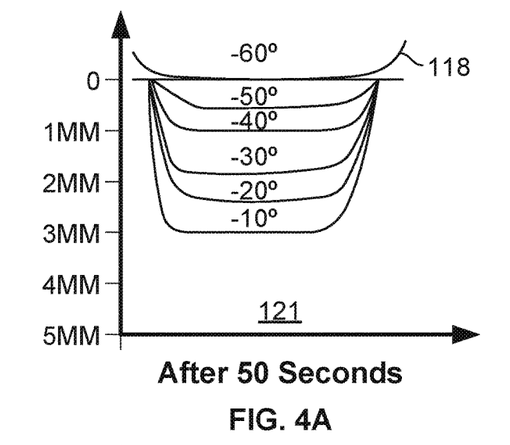
FIGS. 4A-4I illustrate example thermal profiles of the body tissue shown in FIG. 3.
Figure 4B:
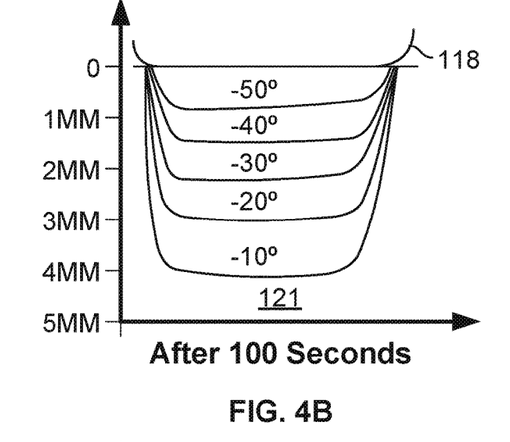
Figure 4C:
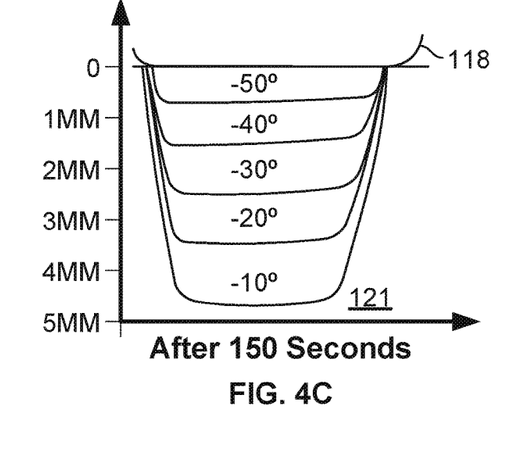

FIGS. 4A-4I illustrate various thermal profiles over time corresponding to different temperatures on the surface 118 of the balloon 103. In particular, FIGS. 4A-4C illustrate simulated isotherms for human body tissue 5 mm in thickness at 50, 100, and 150 seconds after a −60° C. object (e.g., the cryotherapy balloon 103) is brought into contact with the tissue. As depicted in these figures, a cold front moves deeper into the tissue as time progresses. Thus, as shown in FIGS. 4A-4C, after 50 seconds of being in contact with a −60° C. object, tissue 3 mm deep is likely to be at −10° C., and a −20° C. front is likely to have penetrated about 2.4 mm; after 100 seconds, the −10° C. front is likely to have penetrated about 4.1 mm, and the −20° C. front is likely to have penetrated 3 mm; after 150 seconds, almost all of the 5 mm thick tissue (about 4.8 mm) is likely to be at −10° C., and the 20° C. front is likely to have penetrated 3.6 mm. Isotherms for other temperatures are also shown for reference to depict the progressive cooling of the body tissue 121 over time.

Turning briefly to the physiology of cryotherapy, different therapeutic results may be achieved by different levels of cooling. For example, with respect to treating atrial fibrillation by remodeling tissue of the pulmonary veins (e.g., permanently altering the electrical structure or characteristics), it may be desirable to bring tissue over the full thickness of the portion of the pulmonary vein being treated to about −20° C. or colder. A typical human pulmonary vein may have a thickness in the range of 1-5 mm, so a physician may deliver cryotherapy to the pulmonary vein until it is expected that the entire thickness has reached the desired temperature (e.g., −20° C.). The temperature of −20° C. is merely provided as an example. Some tissue may be remodeled, or partially remodeled, at a higher temperature, such as −10° C., but the physician may treat beyond the temperature at which remodeling begins in order to increase the efficacy of the treatment. Other kinds of tissue may be remodeled or otherwise treated at different temperatures.

At higher temperatures (e.g., −5° C., 0° C., 5° C., or some other hypothermic value), a temporary, reversible change in the body tissue may occur. For example, with respect to the aberrant electrical pathways that can give rise to atrial fibrillation, tissue through which the electrical pathways form can be chilled to a temperature that does not permanently remodel the tissue but that temporarily disrupts the electrical pathways. This chilling, which may be referred to as cryomapping, can be used to confirm that remodeling of the intended treatment site will be efficacious, without causing other adverse side effects (e.g., a conduction block in an undesirable location). Following confirmation (e.g., through the use of electrical probes and/or stimuli), the tissue can be permanently remodeled by being cooled to lower temperatures (e.g., −10° C., −20° C., or lower temperatures).

Figure 4D:
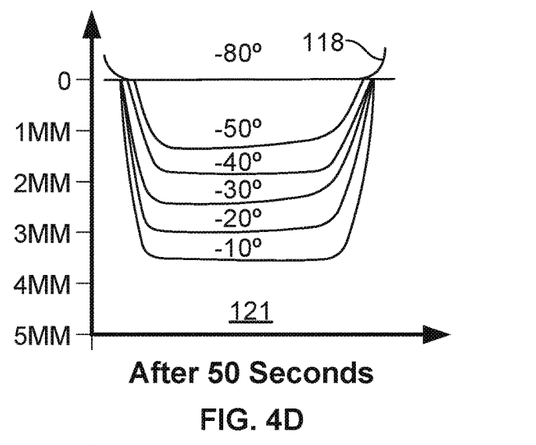
Figure 4E:
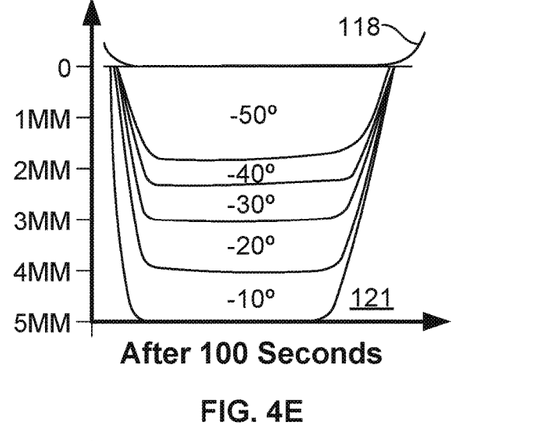
Figure 4F:
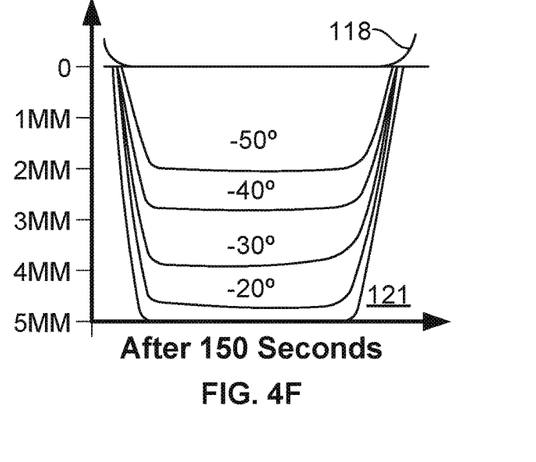
Figure 4G:
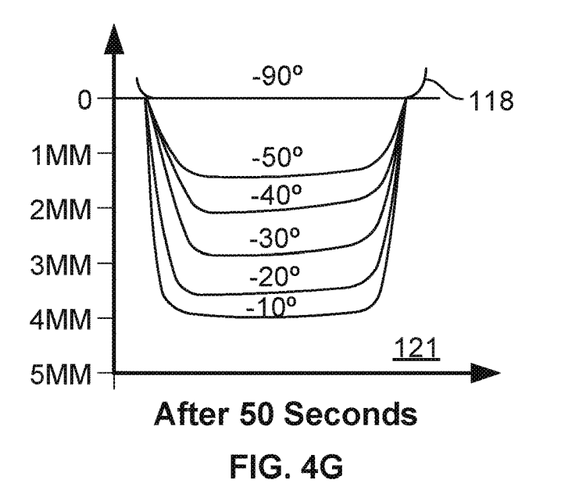
Figure 4H:
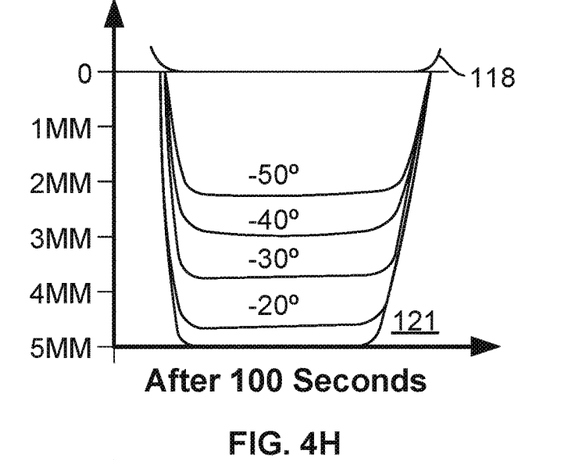
Figure 4I:
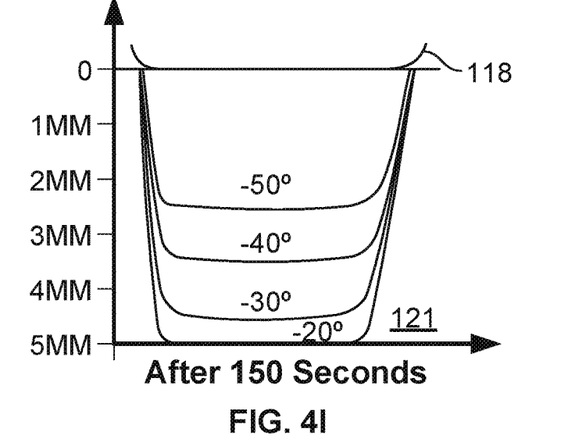

FIGS. 4D-4F illustrate simulated isotherms for human body tissue 5 mm in thickness at 50, 100, and 150 seconds after a −80° C. object (e.g., a cryotherapy balloon) is brought into contact with the tissue. In these figures, the cold front moves through the tissue 121 at a faster rate than the cold front moves in the implementation depicted in FIGS. 4A-4C. In particular, after 50 seconds of being in contact with a −80° C. object, tissue 3.7 mm deep is likely to be at −10° C., and a −20° C. front is likely to have penetrated about 3.1 mm; after 100 seconds, the −10° C. front is likely to have penetrated about 4.1 mm, and the −20° C. front is likely to have penetrated 4.2 mm; after 150 seconds, almost all of the 5 mm thick tissue (about 4.8 mm) is likely to be at −20° C. FIGS. 4G-4I depict an even faster cooling rate that may result when the surface 118 of the balloon 103 is at about −90° C. In particular, a −20° C. cold front may penetrate the tissue 121 to a depth of 3.5 mm, 4.5 mm and more than 5 mm after 50, 100, and 150 seconds respectively.

As can be seen from FIGS. 4A-4I, a cryotherapy procedure can be accelerated by lowering the temperature at the surface 118 of the balloon 103. For a procedure in which it is desirable to cool tissue 5 mm thick to a temperature of −20° C., comparison of FIGS. 4B and 4H reveal differences in treatment time—in FIG. 4H, almost the entire thickness of the tissue is treated after 100 seconds, while in FIG. 4B, the tissue is treated only to about 60% of the desired depth. Additional data related to treatment times is presented in a slightly different format in FIG. 5.

Figure 5:
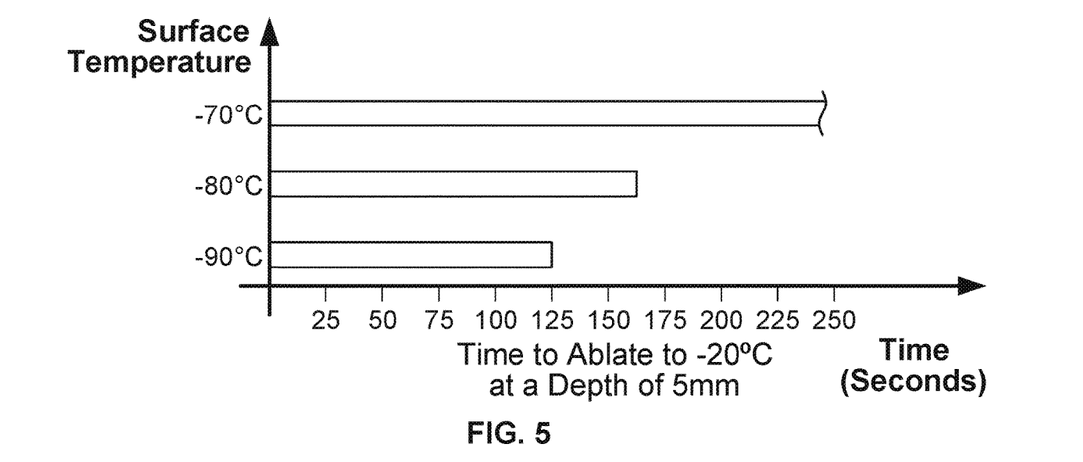
FIG. 5 is a bar graph depicting times that may be necessary for the body tissue shown in FIG. 3 to be ablated to a predetermined depth.

FIG. 5 is a bar graph depicting time (in seconds) that may be necessary for certain body tissue to be ablated to a depth of 5 mm, by a cryotherapy device having a particular surface temperature. As depicted, a cryotherapy device having a surface temperature of −70° C. may require more than 250 seconds to ablate tissue to a depth of 5 mm. In comparison, tissue may be ablated to a depth of 5 mm within 150-175 seconds by a cryotherapy device having a surface temperature of −80° C., and this time may be reduced to about 125 seconds when the cryotherapy device has a temperature of about −90° C. Thus, as depicted in FIG. 5, time needed to ablate tissue to a particular therapeutic depth (e.g., 5 mm)

can be reduced by reducing the temperature of the device that is in contact with the tissue.

One way to reduce the temperature of the device that delivers the cryotherapy is to reduce the pressure inside the device, as is described above with reference to FIGS. 1A, 1B, 2, and 3. When the device is an inflatable cryotherapy balloon, the pressure can be reduced in a second treatment phase, after the tissue to be treated is frozen to the outside of the balloon during a first treatment phase, as described above.

Various advantages may result from accelerating a cryotherapy procedure by reducing the temperature of the cryotherapy device, such as a balloon, used to deliver the cryotherapy. In general, for example, it is advantageous to minimize procedure time for reasons of safety. The longer a procedure lasts, the greater risk there may be for complications, such as internal clotting, structural damage to tissue or organs that are not directly treated but that may be affected by the treatment device (e.g., vessels and heart structures through which a cryotherapy catheter may pass in order to reach specific treatment sites), physician fatigue, etc.

In the case of cryotherapy delivered by a balloon catheter and for the purpose of treating atrial fibrillation, even small reductions in treatment time of a region of tissue may significantly reduce overall treatment time for a procedure. For example, a cryotherapy procedure to treat atrial fibrillation may involve treatment of multiple pulmonary veins (e.g., all four pulmonary veins that are typically present in a human patient), and each pulmonary vein may be treated multiple times (e.g., two times) to increase efficacy of the treatment. Accordingly, even a small improvement of treatment time of a single region of tissue, when multiplied by eight separate treatment cycles, may appreciably reduce the overall treatment time required for the cryotherapy procedure.

Cryotherapy procedures involving inflatable cryotherapy balloons may be particularly advantageous relative to other methods of ablating tissue. For example, some cryotherapy devices enable physicians to first perform cryomapping on target tissue to confirm that permanently ablating the tissue will bring about therapeutic results (e.g., reduce or eliminate aberrant electrical pathways) without causing undesirable collateral damage (e.g., a conduction block). Other techniques may not permit such confirmation testing that is possible with cryotherapy techniques. Delivery of cryotherapy with an inflatable balloon can also be advantageous, since a balloon may conform to multiple differently shaped or sized regions or vessels, and may deliver cryotherapy to an entire circumferential region at one time.

Figure 6:
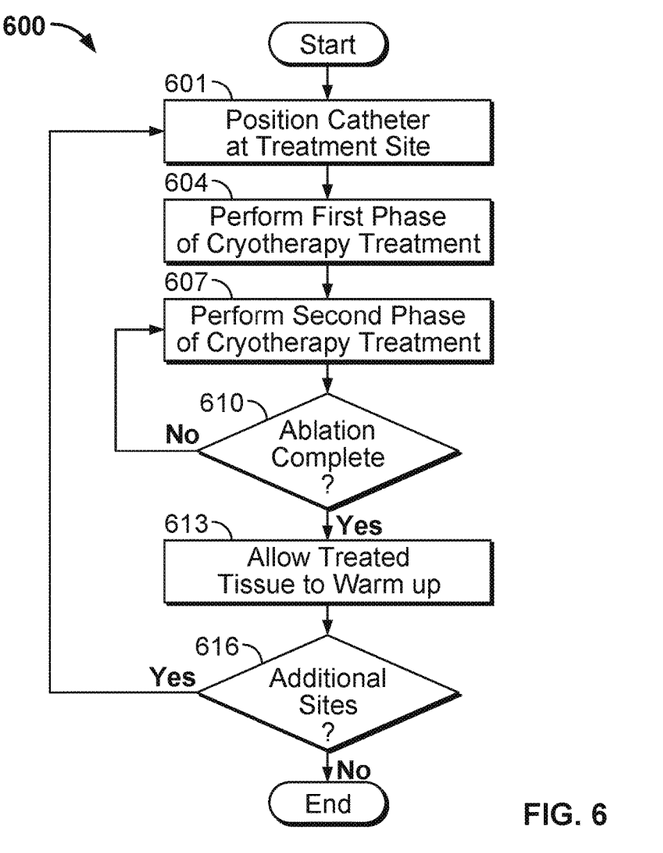
FIG. 6 is a flow diagram illustrating an example method of treating body tissue with the cryotherapy balloon catheter of FIGS. 1A and 1B.

FIG. 6 is a flow diagram illustrating an example method 600 of treating body tissue with the cryotherapy balloon catheter 100. As shown in one implementation, and with reference to the preceding figures, the method 600 can include positioning (601) the cryotherapy balloon 103 at a treatment site inside a patient's body. For example, with reference to a procedure to treat atrial fibrillation, a cryotherapy catheter can be introduced to a patient's left atrium—and more particularly to the ostium of one of the patient's pulmonary veins—by being introduced into the patient's femoral artery, routed through the inferior vena cava, into the right atrium, through the transseptal wall, and into the left atrium (above-referenced anatomic features not shown in the figures).

Once the balloon 103 is positioned (601), a first treatment phase of a cryotherapy procedure can be performed (604). In particular, flow of cryogenic fluid to and flow of exhaust from the chamber 115 of the balloon 103 (see, e.g., FIG. 1A) can be regulated (e.g., by a controller, valves, and/or pumps, as described below with reference to FIG. 7) such that a first pressure inside the chamber 115 is reached that causes the balloon 103 to inflate and firmly impinge on tissue 121 to be treated. Within the chamber 115, cryogenic fluid can be released and changed into a gas, resulting in Joule-Thomson cooling of the chamber 115, the surface 118 of the balloon, and the body tissue 121 that is in contact with the surface. During the first treatment phase, the body tissue 121 can freeze to the surface 118 of the balloon.

Once the tissue 121 freezes to the surface 118 of the balloon 103, a second phase of the cryotherapy procedure can be performed (607). In particular, flow of cryogenic fluid to and flow of exhaust from the chamber 115 of the balloon 103 (see, e.g., FIG. 1B) can be regulated such that a second pressure inside the chamber 115 is reached, which is lower than the first pressure. This second, lower pressure is possible because of a layer of ice 127 between the tissue 121 and the surface 118 of the balloon 103 that forms during the first treatment phase and adheres the tissue 121 to the surface 118 of the balloon 103. The lower pressure can reduce the boiling point of the cryogenic fluid, resulting in a lower temperature at the surface 118 of the balloon 103 during the second treatment phase.

The second phase of the cryotherapy procedure can be maintained until it is determined (610) that the ablation is complete. In some implementations, the time needed to ablate the tissue 121 is determined (610) based on average thickness of the tissue being treated, heat flow within the tissue 121 (e.g., as modeled and depicted in FIGS. 4A-4I), and temperature of the surface 118 of the balloon 103. For example, the second treatment phase may be maintained for about 125 seconds to treat a pulmonary vein that is likely to be about 5 mm thick (e.g., the pulmonary vein of a large adult), when a pressure is reached inside the chamber 115 that is low enough to allow the temperature at the surface 118 to reach −90° C.

Once an ablation cycle is determined (610) to be complete for a particular region of tissue 121, the tissue 121 can be allowed to warm up (613). In particular, for example, flow of cryogenic fluid to an exhaust from the chamber 115 can be regulated (e.g., decreased) such that only a small amount of heat (if any) is extracted from the surface 118 of the balloon, during which time, natural processes can warm the tissue 121 back up (e.g., blood perfusion, heat conducted from adjacent tissue that has not been cooled, heat released from metabolic processes in the cooled or adjacent tissue, etc.).

When the tissue is sufficiently warm, it may no longer adhere to the surface 118 of the balloon 103. That is, the process of warming can result in the layer of ice 127 melting. Once the ice 127 melts, the balloon 103 can be repositioned (601) at another site, and the process can be repeated, if desired. In particular, for example, the balloon 103 can be deflated (e.g., by stopping the flow of cryogenic fluid to the chamber 115 and briefly continuing the flow of exhaust from the chamber 115) and steered (601) to another pulmonary vein, where the first and second phases of cryotherapy treatment can be repeated (604, 607).

Once cryotherapy treatment has been delivered to all desired sites (e.g., all four pulmonary veins, multiple times at each vein), the cryotherapy catheter 100 can be removed from the patient. That is, the balloon 103 can be deflated, and the cryotherapy catheter 100 can be withdrawn back through the septal wall, right atrium, inferior vena cava, and out the femoral artery. This path is merely exemplary, and the reader will appreciate that the cryotherapy catheter can be positioned at any desired treatment site, via any appropriate path.

Additional details of the example cryotherapy catheter 100 are now described with reference to FIG. 7. As described above, the cryotherapy catheter 100 includes an elongate member 109 that has an inflatable balloon 103 at a distal end 706. The balloon 103 has an internal chamber (not shown in FIG. 7, but shown in FIGS. 1A and 1B and referred to in this description as chamber 115) to which cryogenic fluid is delivered to cool the internal chamber, the external surface 118 of the balloon 103, and adjacent body tissue. A port device 702 is attached to the proximal end 106 of the elongate member 109. The port device 702 provides connections to various external equipment, including a cryogenic fluid source 730 and an exhaust pump 727.

Figure 7:
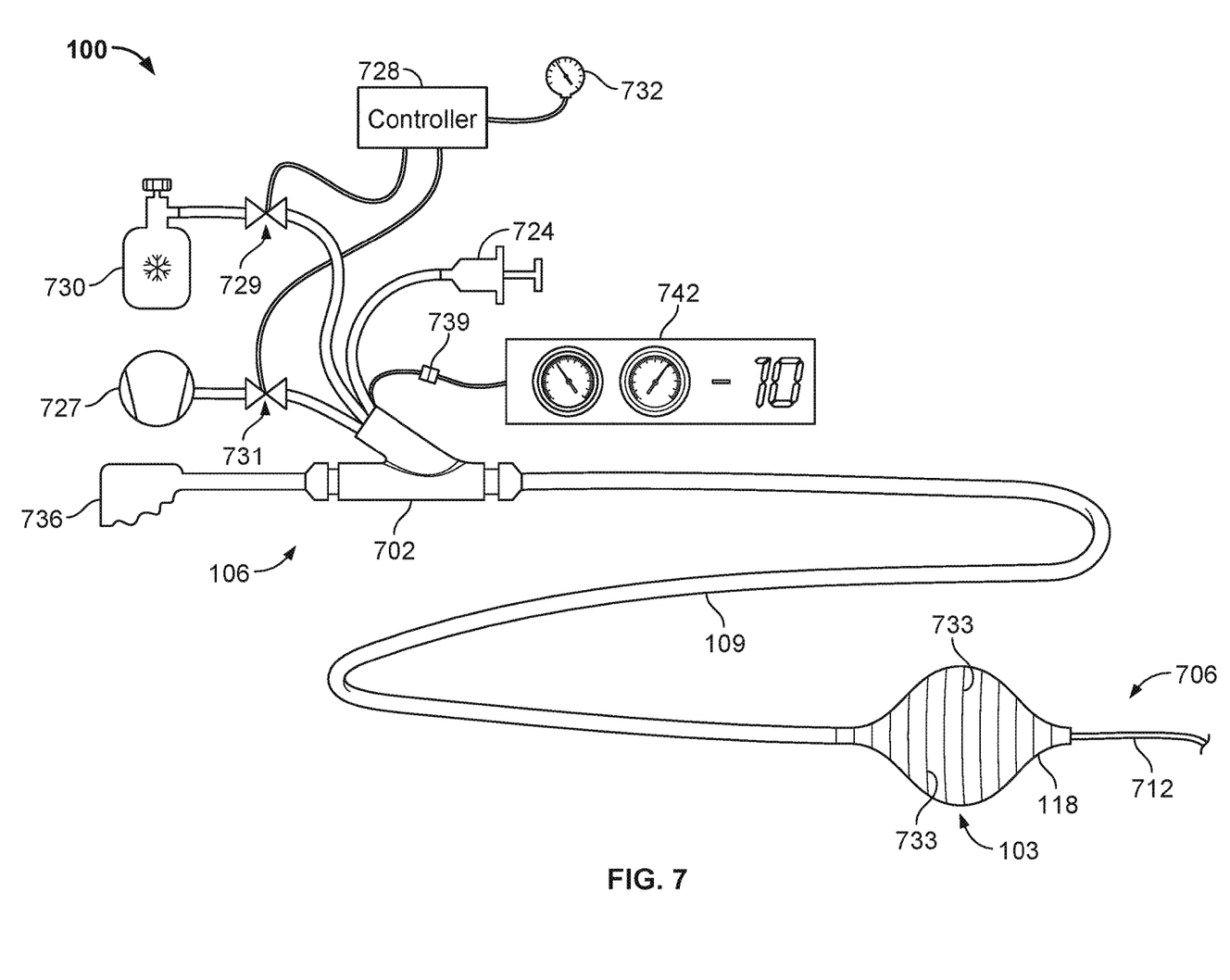
FIGS. 7 and 8A-8C illustrate additional details of the cryotherapy balloon catheter of FIGS. 1A and 1B.

The catheter's elongate member 109 has multiple internal lumens (not shown in FIG. 7). The lumens allow cryogenic fluid to be delivered distally from the external cryogenic fluid source 730 to the internal chamber of the balloon 103. In addition, the internal lumens of the elongate member 109 allow exhaust resulting from delivery of cryogenic fluid to the internal chamber 115 of the balloon 103 to be delivered proximally from the internal chamber 115 to the external exhaust pump 727. During operation, there may be continuous circulation within the elongate member 109 of cryogenic fluid distally and exhaust proximally.

A controller 728 can regulate flow of cryogenic fluid to the internal chamber of the balloon 103 and flow of exhaust from the balloon. In particular, for example, the controller 728 can, in one implementation as shown, regulate a valve 729 that controls flow of the cryogenic fluid from the cryogenic fluid source 730. The cryogenic fluid source 730 may be, for example, a pressured flask of cryogenic fluid. In other implementations (not shown), the controller controls a pump and/or pump valve combination to deliver cryogenic fluid to the internal chamber of the balloon. Similarly, the controller 728 can regulate a valve 731 and/or vacuum pump 727 to regulate flow of exhaust from the internal chamber of the balloon.

By controlling both the rate at which cryogenic fluid is delivered to the balloon 103 and the rate at which exhaust is extracted from the balloon 103, the controller 728 can develop and maintain a pressure inside the balloon 103 at a number of different values. For example, when cryogenic fluid is delivered at a very low rate to the balloon 103, and exhaust is similarly extracted at a very low rate, the balloon 103 may be inflated, but very little heat (if any) may be extracted from the balloon 103 or from body tissue that is in contact with the balloon. As another example, when cryogenic fluid is delivered at a higher rate, a greater amount of heat can be extracted from the balloon 103 and from body tissue that is in contact with the balloon. Varying the rate at which exhaust is extracted from the balloon 103 relative to the rate at which the cryogenic fluid is supplied to the balloon can control the pressure. In particular, for example, for a given rate at which the cryogenic fluid is supplied to the balloon, a greater rate at which exhaust is extracted from the balloon 103 will generally result in lower pressure inside the balloon, and a lower rate at which exhaust is extracted from the balloon 103 will generally result in greater pressure inside the balloon.

To precisely control pressures or flow rates, the controller 103 may employ either or both of open- or closed-loop control systems. For example, in some implementations, a rate at which cryogenic fluid (e.g., the position of the valve 729) may be controlled with an open-loop control system, and a rate at which exhaust is extracted from the balloon 103 (e.g., the position of the valve 731 or force exerted by the pump 727) may be controlled with a closed-loop control system. In other implementations, both rates may be controlled by closed-loop control systems. In a closed-loop control system, some feedback mechanism is provided. For example, to control the rate at which exhaust is extracted from the balloon 103, the controller 728 may employ an exhaust flow device (not shown), a pressure sensor (not shown) inside the balloon 103 or elsewhere in the system, or another feedback sensor. In addition, the controller 728 may employ an ambient pressure gauge 732 in one of its control loops (e.g., to measure atmospheric pressure at the proximal end 106 of the cryotherapy catheter (that is, the end that remains outside the patient)).

In some implementations, as mentioned above, pressure inside the balloon 103 may be primarily controlled by controlling the rate at which exhaust is extracted from the balloon 103 (given the significant difference between the large volume of gas resulting from a corresponding smaller volume of cryogenic fluid being released into the balloon 103). Temperature inside the balloon 103, on the other hand, may depend on control of both the flow of cryogenic fluid and the flow of exhaust.

The controller 728 itself can take many different forms. In some implementations, the controller 728 is a dedicated electrical circuit employing various sensors, logic elements, and actuators. In other implementations, the controller 728 is a computer-based system that includes a programmable element, such as a microcontroller or microprocessor, which can execute program instructions stored in a corresponding memory or memories. Such a computer-based system can take many forms, may include many input and output devices, and may be integrated with other system functions, such as the monitoring equipment 742, a computer network, other devices that are typically employed during a cryotherapy procedure, etc. For example, a single computer-based system may include a processor that executes instructions to provide the controller function, display imaging information associated with a cryotherapy procedure (e.g., from an imaging device); display pressure, temperature, and time information (e.g., elapsed time since a given phase of treatment was started); and serve as an overall interface to the cryotherapy catheter. In general, various types of controllers are possible and contemplated, and any suitable controller 728 can be employed.

The catheter 100 shown in FIG. 7 is an over-the-wire type catheter. Such a catheter 100 uses a guidewire 712, extending from the distal end 706 of the catheter 100. In some implementations, the guidewire 712 may be pre-positioned inside a patient's body. Once the guidewire 712 is properly positioned, the balloon 103 (in a deflated state) and the elongate member 109 can be routed over the guidewire 712 to a treatment site. In some implementations, the guidewire 712 and balloon portion 103 of the catheter 103 may be advanced together to a treatment site inside a patient's body, with the guidewire portion 712 leading the balloon 103 by some distance (e.g., several inches). When the guidewire portion 712 reaches the treatment site, the balloon 103 may then be advanced over the guidewire 712 until it also reaches the treatment site. Other implementations are contemplated, such as steerable catheters that do not employ a guidewire.

The catheter 100 includes a manipulator 736, by which a medical practitioner may navigate the guidewire 712 and balloon 103 through a patient's body to a treatment site. In some implementations, release of cryogenic fluid into the cooling chamber may inflate the balloon 103 to a shape similar to that shown in FIG. 7. In other implementations, a pressure source 724 may be used to inflate the balloon 103 independently of the release of cryogenic fluid into the internal chamber 115 of the balloon 103. The pressure source 724 may also be used to inflate an anchor member on the end of the guidewire 712 (not shown).

The catheter 100 includes a connector 739 for connecting monitoring equipment 742. The monitoring equipment may be used, for example, to monitor temperature or pressure at the distal end of the catheter 100. To aid in positioning the treatment member 103 of the catheter 100 inside a patient's body, various marker bands 733 are also disposed at the distal end 706 of the catheter 100. The marker bands 733 may be opaque when the catheter is viewed by x-ray or other imaging techniques.

In some implementations, the balloon 103, and a corresponding separate internal cooling chamber, if present (e.g., balloon 821, shown in FIG. 8A), may be formed from a polymer including, but not limited to, polyolefin copolymer, polyester, polyethylene teraphthalate, polyethylene, polyether-block-amide, polyamide (e.g., nylon), polyimide, latex, or urethane. For example, certain implementations of the balloon 103 comprise PEBAX® 7033 material (70D poly ether amide block). The balloon 103 may be made by blow-molding a polymer extrusion into the desired shape. In some implementations, the balloon 103 may be constructed to expand to a desired shape when pressurized without elastically deforming substantially beyond the desired shape.

A number of ancillary processes may be used to affect the material properties of the balloon 103. For example, the polymer extrusion may be exposed to gamma radiation which can alter the polymer infrastructure to provide uniform expansion during blow molding and additional burst strength when in use. In addition, the molded balloon 103 may be exposed to a low temperature plasma field which can alter the surface properties to provide enhanced adhesion characteristics. Those skilled in the art will recognize that other materials and manufacturing processes may be used to provide balloon 103 (and any internal balloon(s)) suitable for use with the catheter.

Figure 8A:
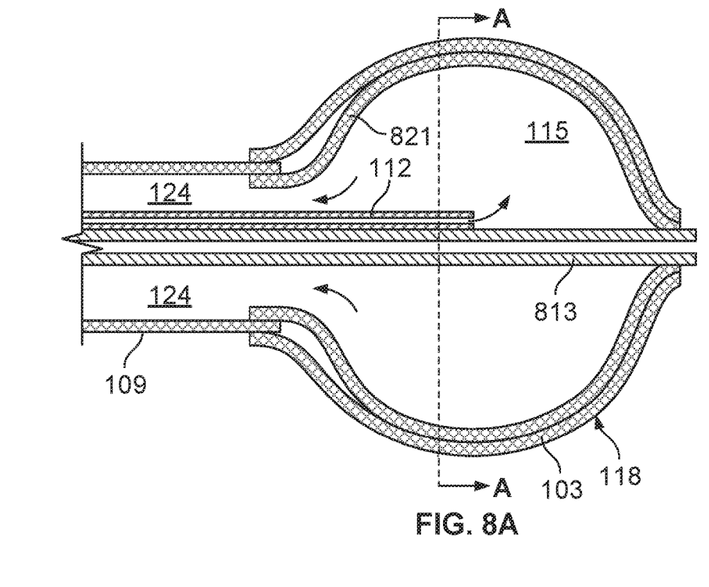

FIG. 8A shows a longitudinal cross-section of the example cryotherapy balloon 103 and an example elongate member 109 through which cryogenic fluid and exhaust may be cycled to and from the internal chamber 115 of the cryotherapy balloon 103. As shown in FIG. 8A, cryogenic fluid may be delivered from an external source (e.g., 730 in FIG. 7) to a cooling chamber 115 internal to the balloon 103, via a coolant delivery lumen 112. The coolant may be released into the cooling chamber 115 from an opening at the end of the delivery lumen 112, or the coolant may be released through a cryotherapy device 819 (see FIG. 8C) disposed at the end of the delivery lumen 112. In some implementations, the cooling device 819 includes a coiled extension 835 having a number of apertures 837 from which pressurized liquid coolant can escape and change state to a gas. In some implementations, the exhaust lumen 124 may be defined generally by the outer layer of the elongate shaft 109, as shown. In other implementations, the catheter may include one or more dedicated exhaust lumen structures (not shown) that are defined independently of the elongate member 109.

In some implementations, as described above, the coolant undergoes a phase change within the cooling chamber 115, cooling the chamber 115 via the Joule-Thomson effect, as well as cooling the external surface 118 of the outermost balloon 103 and a patient's body tissue that is adjacent to the external surface 118 of the outer balloon. In other implementations, cryogenic fluid is applied to (e.g., sprayed against) the walls of the cooling chamber, where it vaporizes, directly cooling the chamber wall and the external surface 118. The cryogenic fluid, or gas if the fluid has undergone a phase change, is then exhausted through an exhaust lumen 124 to a reservoir, pump, or vacuum source external to the catheter (e.g., 727 in FIG. 7). In some implementations, there is a continuous cycle of cryogenic fluid to the cooling chamber 115 via the delivery lumen 112 and exhaust from the cooling chamber 115 via the exhaust lumen 124.

The coolant that is cycled into the balloon 115 is one that will provide the appropriate heat transfer characteristics consistent with the goals of treatment. In some implementations, liquid $N_2O$ may be used as a cryo coolant. When liquid $N_2O$ is used, it may be transported to the cooling chamber 115 in the liquid phase where it changes to a gas at the end of the coolant delivery lumen 112, or from the apertures 837 of a cooling device 819. Other implementations may use Freon, Argon gas, and $CO_2$ gas, or other agents, as coolants. Still other implementations may use liquid coolant, and the temperature or pressure of the liquid coolant may be controlled in a manner appropriate to achieve the desired therapeutic effect.

In some implementations, as shown, a second balloon 821 is provided within the outer balloon 103 to isolate the cryogenic fluid within the cooling chamber 115. In these implementations, the outer balloon 103 forms a safety chamber that prevents coolant from escaping if the cooling chamber 115 balloon 821 bursts. A separate vacuum lumen (not shown) may be provided to evacuate any gas or liquid that escapes from the internal cooling chamber 115. In operation, the outer and inner balloons 103 and 821 may expand and deflate together. In some implementations, release of coolant inflates the balloons 103 and 821. In some implementations, the balloons 103 and 821 are first inflated by the injection of an inflation fluid or gas (e.g., a saline solution or an inert gas), after which the coolant may be introduced to the cooling chamber 115.

Figure 8B:
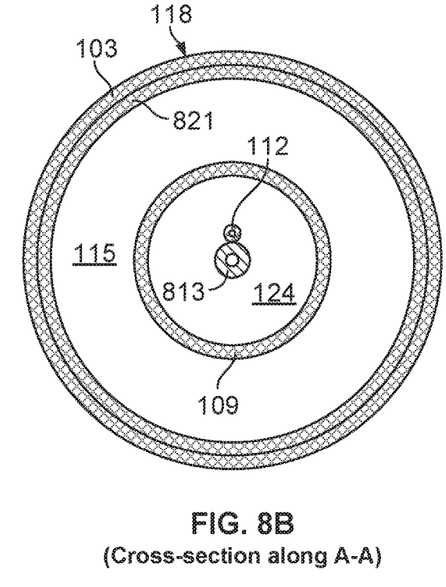
Figure 8C:
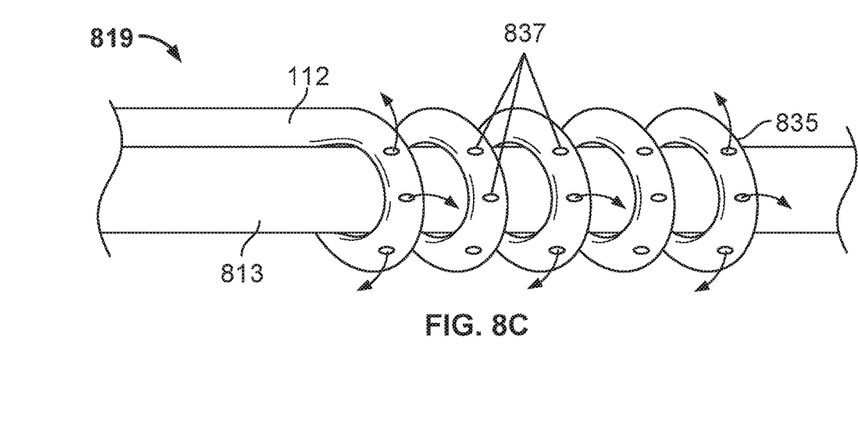

FIG. 8B shows a radial cross-section along the line A-A that is shown in FIG. 8A. As shown in FIG. 8B, the coolant delivery lumen 112 is adjacent to the guidewire lumen 813, and the guidewire lumen 813 is shown to be substantially coaxial with the exhaust lumen 124, which corresponds to the overall shaft (e.g., elongate member 109) of the catheter. In some implementations, lumens may have other arrangements, and more or fewer lumens may be included in the catheter. For example, the coolant delivery lumen 112 may be disposed coaxially around the guidewire lumen 813; the guidewire lumen 813 may be omitted in a steerable catheter design; lumens for steering members may be provided; one or more vacuum lumens may be included; one or more exhaust lumens may be included that are independent of the outer layer of the catheter shaft 109; additional lumens may be provided for inflating or deflating the balloons 103 or 831 or for inflating or deflating other balloons not shown in FIG. 8A; and additional lumens may be provided to control an anchor member that may be disposed on a guidewire near the distal portion of the balloon 103.

Figure 9:
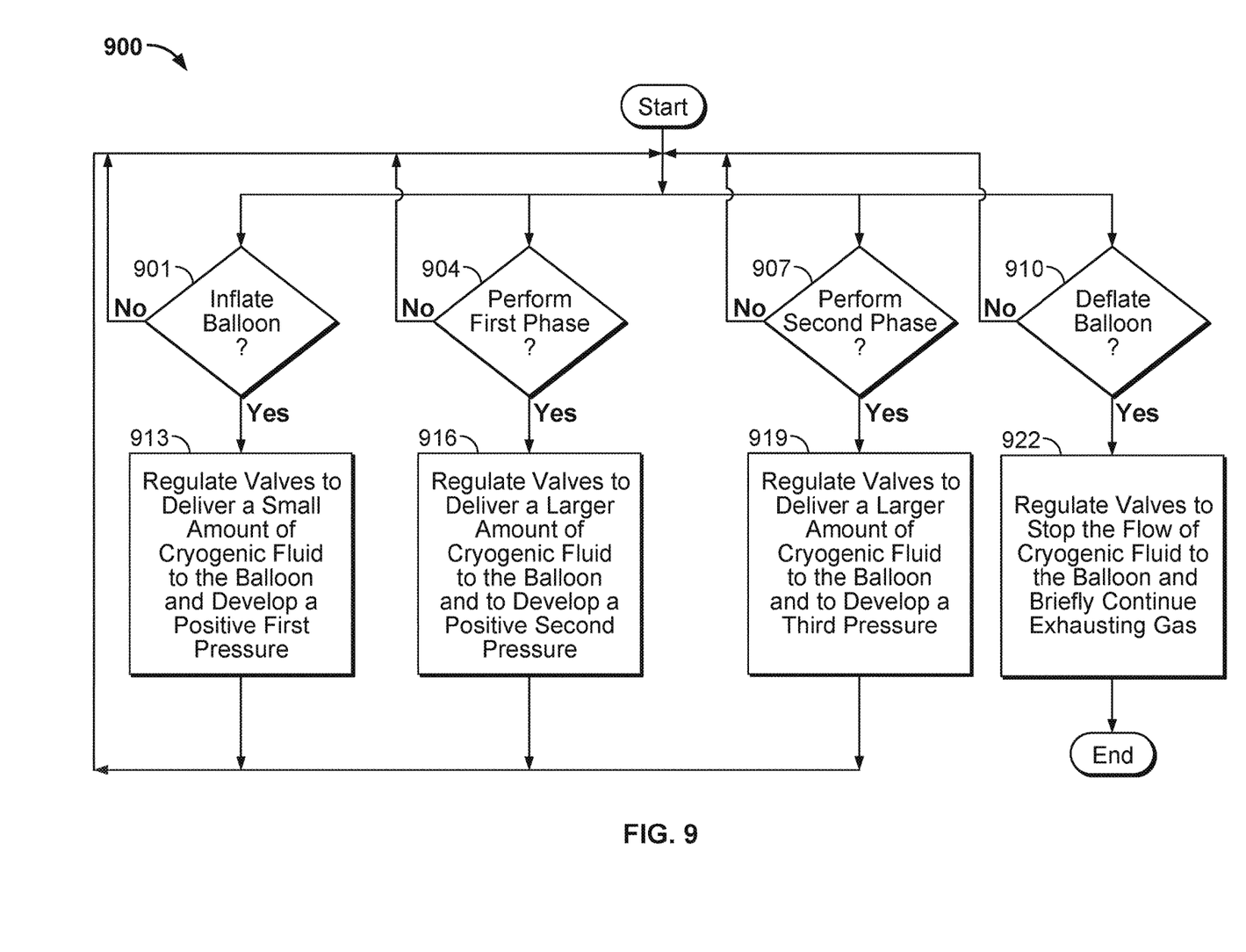
FIG. 9 is a flow diagram illustrating an example method of controlling pressure and temperature in the cryotherapy balloon catheter of FIGS. 1A and 1B.

FIG. 9 is a flow diagram illustrating an example method 900 of controlling pressure and temperature in the balloon 103. In some implementations, the method 900 is implemented by the controller 728 shown in FIG. 7. As shown in one implementation, the method 900 can include various decision elements that determine whether the balloon 103 is to be inflated (901) or deflated (910), whether a first treatment phase is to be performed (904) or whether a second treatment phase is to be performed (907). The decision elements can, in some implementations, be evaluated based on user input received by the controller 728. For example, during a cryotherapy procedure, a physician may provide input to the controller 728 (e.g., through a command entered through a user interface of a computer device, through manual actuation of a switch, etc.) to inflate the balloon or initiate a particular phase of treatment.

When it is determined (901) that the balloon is to be inflated, the controller 728 can actuate (913) appropriate valves (e.g., valves 729 and 731) to deliver a small amount cryogenic fluid to the balloon 103 in order to develop a positive first pressure. In some implementations, a burst of cryogenic fluid is delivered to the balloon 103 to develop the positive first pressure. In other implementations, a low rate of continuous flow of cryogenic fluid is established and an appropriate corresponding low rate of exhaust extraction is also established through control of the valves 729 and 731, or the valve 729 and the pump 727. To establish an appropriate flow rate and pressure, the controller 728 may employ the ambient pressure gauge 732, a pressure sensor (not shown in the figures) inside or fluidly coupled to the balloon 103, a balloon position sensor (e.g., imaging tools that detect the outer surface of the balloon 103), etc.

When it is determined (904) that a first phase of treatment is to be initiated, the controller 728 can actuate (916) the valves 729 and 731 to deliver a relatively large flow rate of cryogenic fluid to the balloon (e.g., relative to flow necessary to merely keep the balloon 103 inflated), and to extract a correspondingly large amount of exhaust from the balloon 103. The rates of delivery and extraction can be controlled such that a positive second pressure is developed and maintained inside the balloon. That is, relative to ambient pressure and other compressive forces that may exist at the balloon (e.g., from elastic forces of the balloon itself or from compressive forces exerted by tissue of the body lumen or cavity being treated), a positive pressure inside the balloon 103 may be developed, such that the balloon 103 is inflated and firmly in contact with adjacent body tissue. With such firm contact, high flow rate of cryogenic fluid to the balloon, and the resulting low temperature caused by the Joule-Thomson expansion of the cryogenic fluid to a gas inside the balloon, tissue that is adjacent to the balloon 103 can freeze to the surface of the balloon 103.

When it is determined (907) that a second phase of treatment is to be initiated, the controller 728 can actuate (919) the valves 729 and 731 to deliver a similar rate of cryogenic fluid to the balloon that was delivered in the first phase (916), but the rate at which exhaust is extracted can be slightly increased, to develop a third pressure that is lower than the second pressure. That is, the valve 731 can be opened slightly, or the force exerted by the vacuum pump 727 can be increased slightly, resulting in a lower pressure inside the balloon. As described above, this lower pressure can result in a lower boiling temperature of the cryogenic fluid inside the balloon 103 and a corresponding lower temperature on the surface of the balloon 103.

When it is determined (910) that the balloon is to be deflated, the controller 728 can actuate (922) the valves such that flow of cryogenic fluid to the balloon 103 is stopped, and flow of exhaust from the balloon 103 is briefly continued. Continuation of the flow of exhaust (e.g., by closing the valve 731 after the valve 729), can create a vacuum inside the balloon 103 that can draw the material of the balloon 103 radially inward, toward a central axis of the balloon 103. After the balloon is deflated, it can be removed from the patient in any appropriate manner.

The above description makes reference to controlling valves 729 and 731 by way of example, but the reader will appreciate that various other methods of controlling flow to and from the balloon 103 can be employed, including, for example, controlling the pump 727, or controlling other pumps or valves that are not shown in the figures but that may be included in cryotherapy catheter systems.

A number of implementations have been described. Nevertheless, it will be understood that various modifications may be made without departing from the spirit and scope of this document. Accordingly, other implementations are within the scope of the following claims.

What is claimed is:

1. A method of operating a cryotherapy balloon catheter, the method comprising:
    introducing a cryotherapy balloon catheter to a treatment site inside a patient's body, the cryotherapy balloon catheter including an inflatable balloon at a distal end of an elongate member, the elongate member having lumens therein configured to supply cryogenic fluid to the balloon;
    creating a first pressure with cryogenic fluid inside the balloon that is above ambient pressure, wherein ambient pressure comprises atmospheric air pressure adjacent to the patient's body, thereby freezing an outer wall of the balloon against body tissue at the treatment site; and
    thereafter, creating a second pressure inside the balloon, wherein the second pressure is equal to or negative relative to the ambient pressure and is sufficient to prevent the outer wall from being peeled away from the body tissue by vacuum forces inside the balloon or by elastic forces of material that makes up the balloon.

2. The method of claim 1, wherein the cryotherapy balloon catheter is configured to enable Joule-Thomson cooling inside the balloon.

3. The method of claim 1, wherein the first pressure is approximately five pounds per square inch (PSI) above ambient pressure.

4. The method of claim 1, wherein the first pressure is approximately 5-25 pounds per square inch (PSI) above ambient pressure.

5. The method of claim 1, wherein a first temperature at the first pressure is above a second temperature at the second pressure.

6. The method of claim 5, wherein the first temperature is less than 0° C.

7. The method of claim 6, wherein the second temperature is between −89° C. and −91° C.

8. The method of claim 1, wherein creating the second pressure extracts heat from the body tissue at a greater rate than a rate at which heat is extracted from the body tissue at the first pressure.

9. The method of claim 1, further comprising deflating and removing the balloon from the treatment site.

10. The method of claim 9, further comprising introducing the cryotherapy balloon to a second treatment site, and repeating the steps of creating the first and second pressures to repeat the cryotherapy procedure at the second treatment site.

11. The method of claim 1, wherein creating the first and second pressures comprises regulating flow of liquid nitrous oxide into the balloon and flow of gaseous nitrous oxide out of the balloon.

12. The method of claim 1, wherein creating the first pressure includes supplying cryogenic fluid to the balloon such that the cryogenic fluid boils at a first temperature in an environment of the first pressure, and boils at a second temperature, which is lower than the first temperature, at pressures that are less than the second pressure.

13. The method of claim 1, wherein creating the first and second pressures is achieved by regulating a flow of cryogenic fluid into and exhaust from the balloon.

14. The method of claim 1, wherein the second pressure is negative relative to the ambient pressure.

15. The method of claim 1, wherein the second pressure is maintained until ablation of the body tissue at the treatment site is complete.

16. The method of claim 15, wherein the second pressure is maintained for at least 25 seconds.

* * * * *